United States Patent [19]
Makita et al.

[11] Patent Number: 5,609,564
[45] Date of Patent: Mar. 11, 1997

[54] SPECULUM COVER, METHOD OF MANUFACTURING SAME AND COVER ACCOMMODATING CASE

[75] Inventors: Shigeru Makita; Yoshihiko Sano; Hiroyuki Ota, all of Kyoto, Japan; Yasushi Nakamura, Irvine, Calif.

[73] Assignee: Omron Corporation, Kyoto, Japan

[21] Appl. No.: 343,440

[22] PCT Filed: Mar. 31, 1993

[86] PCT No.: PCT/JP93/00406

§ 371 Date: Sep. 30, 1994

§ 102(e) Date: Sep. 30, 1994

[87] PCT Pub. No.: WO93/19662

PCT Pub. Date: Oct. 14, 1993

[30] Foreign Application Priority Data

Apr. 1, 1992 [JP] Japan .................. 4-079515
Apr. 6, 1992 [JP] Japan .................. 4-083517

[51] Int. Cl.⁶ ........................................... A61B 1/26
[52] U.S. Cl. .................. 600/200; 600/203; 600/186; 374/158
[58] Field of Search .................. 600/184, 186, 600/200, 203; 206/305, 306; 374/158, 209

[56] References Cited

U.S. PATENT DOCUMENTS

| | | | |
|---|---|---|---|
| 3,469,685 | 9/1969 | Baermann | 206/63.2 |
| 3,878,836 | 4/1975 | Twentier | 600/200 |
| 4,662,360 | 5/1987 | O'Hara et al. | |
| 4,911,559 | 3/1990 | Meyst et al. | 374/158 |
| 5,088,834 | 2/1992 | Howe et al. | 374/158 |
| 5,100,018 | 3/1992 | Rosati et al. | 221/6 |
| 5,163,418 | 11/1992 | Fraden et al. | 600/200 |
| 5,179,936 | 1/1993 | O'Hara et al. | 600/200 |

FOREIGN PATENT DOCUMENTS

| | | |
|---|---|---|
| 0419100A1 | 3/1991 | European Pat. Off. . |
| 0445784 | 9/1991 | European Pat. Off. . |
| 3-133425 | 6/1991 | Japan . |
| 4-502206 | 4/1992 | Japan . |

OTHER PUBLICATIONS

European Search Report dated Jul. 27, 1995 for the corresponding EPC Patent Application No. EP 93 90 6860.

*Primary Examiner*—Richard J. Apley
*Assistant Examiner*—Beverly M. Flanagan
*Attorney, Agent, or Firm*—Fish & Richardson P.C.

[57] ABSTRACT

A sensor probe cover (20) is composed of two substantially square transparent films (21) and (22) and a ring (23) having a hole (23a) suitable for being mated with a sensor probe (12). The center of the first film (21) is provided with a hole (21a), and the ring (23) is fused to the inner periphery of the hole (21a) on the inner surface of the first film (21). The ring (23) is made of a material harder than that of the films. The first film (21) and the second film (22) are thermally fused together at the four corners of these films. The thermally fused locations are indicated at (20a). When used in the cover of the probe of an infrared thermometer, the second film (22) is made of a material transparent to infrared radiation. When the tip of the probe (12) is pressed into the ring (23) from above the second film (22), the probe (12) is covered while the second film (22) is folded back. The fitting on of the cover is completed when the ring (23) fits into an annular groove (12a) of the probe (12).

8 Claims, 14 Drawing Sheets

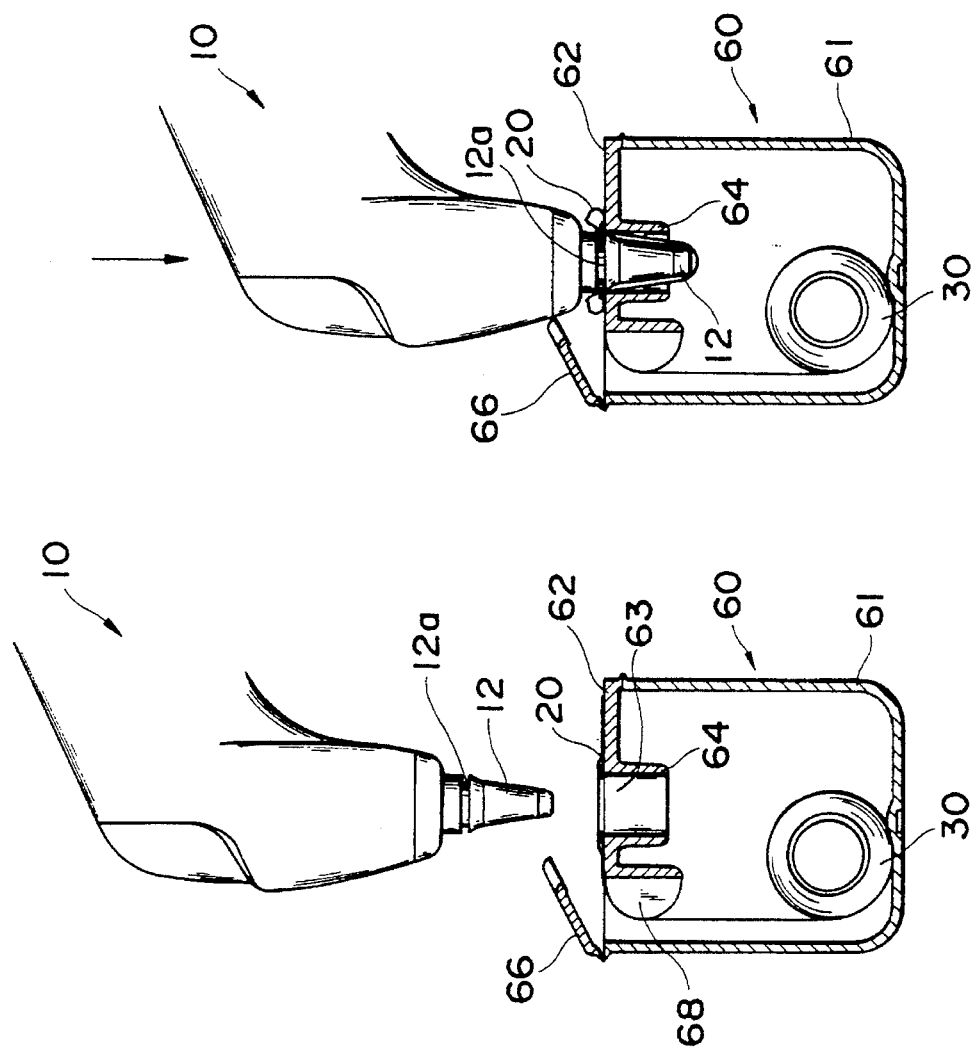

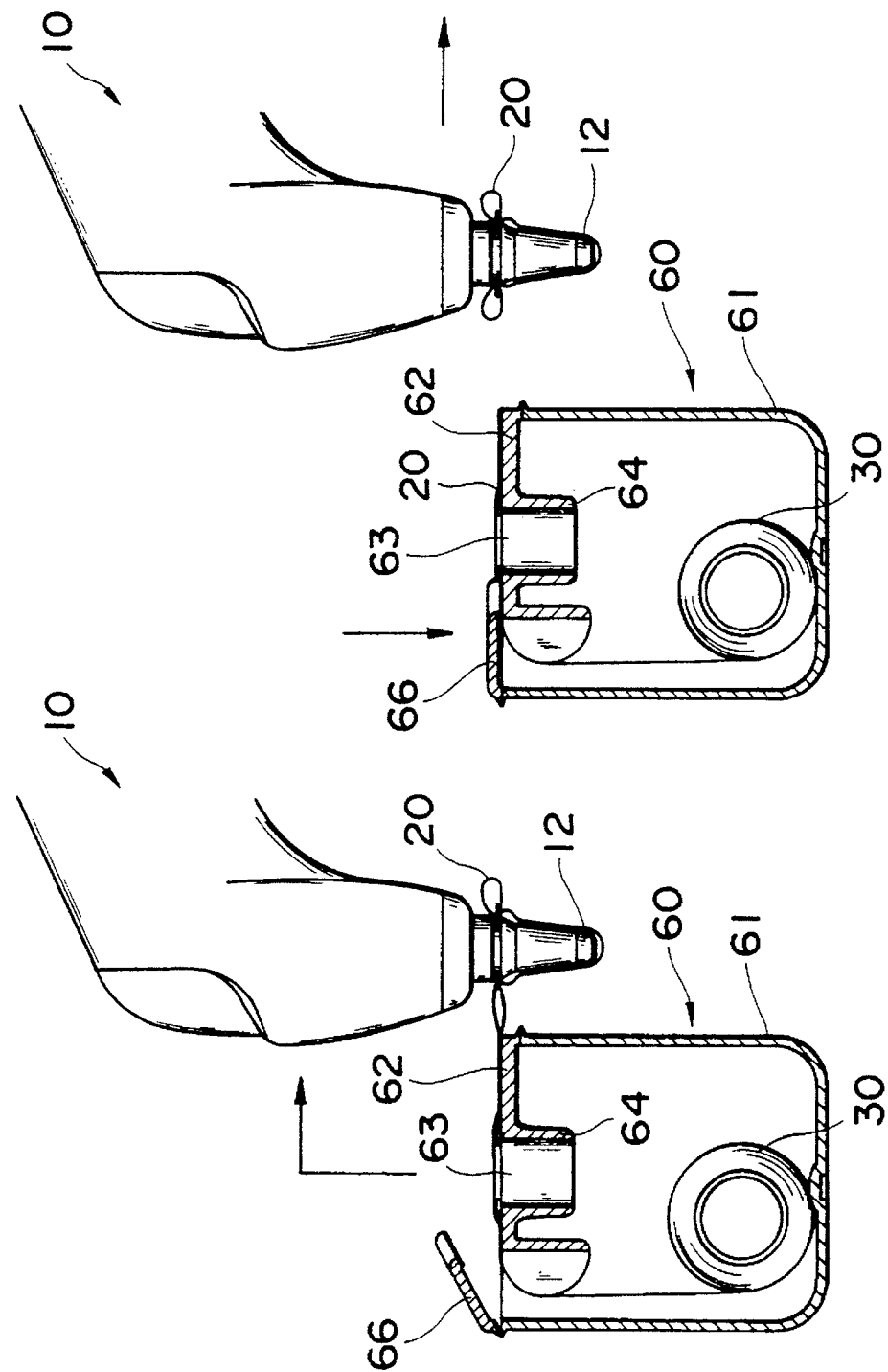

SPECULUM COVER, METHOD OF MANUFACTURING SAME AND COVER ACCOMMODATING CASE

TECHNICAL FIELD

This invention relates to a cover fitted over a sensor probe, particularly a disposable sanitary (for the purpose of preventing infection) cover, a method of manufacturing the cover and a case or stand suitable for use in order to accommodate the cover or for when the cover is attached to the probe. In particular this cover is suitable for a cover fitted over a probe of an infrared thermometer.

BACKGROUND ART

An infrared thermometer is equipped with a probe protruding outwardly from pare of a case body. The distal end of the probe is open and is provided internally with a radiant-energy temperature sensor (a thermopile, for example). When the tip of the probe is inserted slightly into the ear canal, heat rays (infrared rays) emitted from the external ear impinge upon the radiant-energy temperature sensor. The temperature sensor is connected to a temperature measurement circuit provided in the case body. The measurement circuit determines body temperature based upon the output of the temperature sensor. Thus, the infrared thermometer is capable of measuring body temperature in a short period of time basically without making contact (at least the temperature sensor does not contact the human body).

In order to prevent the transmission of various diseases, a sanitary cover is fitted over the tip of the probe of the infrared thermometer at the time of temperature measurement. The sanitary cover is replaced for each individual (patient) subjected to measurement and is discarded after use.

Typical examples of such a cover fitted over the probe of a speculum which includes an infrared thermometer are described in U. S. Pat. No. 4,662,360 and EP-A-419,100.

A sanitary cover described in the former comprises a tubular body and a membrane, which is transparent to infrared radiation, covering an opening at the tip of the tubular body. The tubular body is fabricated by injection molding and the membrane is attached thereto by thermal welding.

The probe cover described in the latter comprises a sheath fitted on a probe and having a closed distal end face serving as a window, and a ring attached to a base end of the sheath by ultrasonic welding and engaged with the probe. The sheath is produced using a forming punch.

Since both covers comprise two individually fabricated parts that are combined, the separate parts are costly and considerable labor is involved in manufacture. An additional problem is low productivity since batch treatment is unavoidable, thus making it impossible to work the covers continuously.

The simplest structure is one in which two small holes are formed in the end or edge of a rectangular or circular film (sheet). The film is used to cover the tip of the probe and is secured by engaging the holes with projection provided on the base end of the probe.

Since this probe cover is such that the holes are merely formed in the film, problems arise in that it is difficult to attach the cover to the probe. Moreover, the film tends to shift from the attached position. If the film shifts or becomes detached, its infection preventing function is lost.

DISCLOSURE OF THE INVENTION

The present invention provides a sensor probe cover capable of being produced inexpensively at a high productivity.

The present invention further provides a sensor probe cover which has a simple structure, is easy to fit over a probe and will not readily become detached.

The present invention further provides a method of manufacturing the above-described sensor probe cover.

The present invention further provides a jig which is ideal when the above-described sensor probe cover is fitted over the probe.

A sensor probe cover according to the present invention comprises a first film formed to have a first hole at a central portion thereof, a fitting ring fixed to a periphery of the first hole of the first film and having a second hole suitable for being fitted on a sensor probe to which the cover is to be attached, and a second film overlapping one side of the first film and bonded to the first film at a plurality of locations.

Here the term "film" is a generic expression indicating a thin, flexible, two-dimensional member of some expanse and is intended to cover the meaning of a member referred to as a sheet or other similar term.

There is no limitation upon the material constituting the first film so long as the first film retains the fitting ring and achieves the function of connecting the fitting ring and the second film.

As will be understood from the method of fitting the cover on the probe described later, the second film penetrates the ring together with the probe so as to cover the tip of the probe when the cover is fitted over the probe. As a result, the material constituting the second film is selected to be one which will readily follow up motion of the probe without tearing.

It is required that the second film be transparent to infrared radiation in order that the probe cover according to the present invention may be made one suitable for being fitted over the sensor probe of an infrared thermometer.

In a case where the probe covers are produced continuously as described later, adopting the same material for both the first and second films is advantageous is terms of cost and ease of manufacture.

The fitting ring is fitted onto the probe at a suitable location and it is so arranged that the cover will not readily become detached from the probe. Accordingly, a material having an appropriate hardness would be selected for the ring. The shape of the ring, especially the shape of the inner periphery thereof, would be decided in conformity with the cross-sectional configuration of the proper probe.

The method of fitting the probe cover over the sensor probe is as follows: The tip of the probe is inserted into the ring, which is provided on the first film, from the side of the second film. When this is done, the second film also is caused to pass through the hole in the ring and is folded over the probe tip by following up the penetrating motion of the probe tip. The fitting on of the probe cover is completed when a suitable location near the base of the probe is fitted into or engaged with the ring. The result is that the tip of the probe is covered by the second film.

The first film also is pulled by the second film and folded back when the second film is folded over the probe tip as the probe penetrates the ring. In order that such deformation of the second and first films may proceed stably and smoothly, it is required that a substantially uniform force act upon the first and second films about the center of the ring.

To this end, in a preferred embodiment of the present invention, the first and second films are bonded at a plurality of locations substantially equidistant from the center of the fitting ring and spaced apart substantially equiangularly. For example, in a case where the first and second films are rectangular (preferably square or nearly square), the films are bonded together at their four corners.

Thus, the probe cover according to the present invention is composed of three parts, namely the first and second films and the fitting ring secured to the first film. Inexpensive materials can be used for each of these parts and the structure of the cover is simple as well. Consequently, the probe cover can be provided at low cost. Moreover, since the cover can be attached to the probe merely by inserting the tip of the probe in the ring, the operation for attaching the cover is simple. Since the ring is fitted onto or engaged with the probe, the cover will not readily fall off.

The present invention provides a chain of interconnected covers in which a plurality of the above-mentioned probe covers are continuously connected in the form of a strip. The chain of interconnected covers comprises a first strip-shaped film in which first holes are formed at regular intervals in a longitudinal direction, each first hole having a fitting ring secured to the periphery thereof, and a second strip-shaped film overlapping the first strip-shaped film and bonded to the first strip-shaped film over a plurality of locations nearly midway between the fitting rings. A portion between bonded locations bracketing a fitting ring constructs one cover.

The chain of interconnected covers can be separated into individual probe covers by severing it at the boundaries between mutually adjacent covers.

Preferably intermittent slits are provided along the boundary lines between covers so that the covers can be easily detached without using a cutting tool such as scissors, a cutter or the like.

The present invention provides a method of manufacturing the chain of interconnected covers described above. The method of manufacture comprises forming first holes in a first strip-shaped film at regular intervals in a longitudinal direction thereof, detachably forming rings in a strip-shaped film for rings at regular intervals in a longitudinal direction thereof, superimposing the first strip-shaped film and the strip-shaped film for rings in such a manner that the rings are situated at the peripheries of the first holes, fixing the rings in the peripheries of the first holes of the first strip-shaped film and detaching the rings from the strip-shaped film for rings, and bonding the first strip-shaped film and the second strip-shaped film at a plurality of locations nearly midway between the fitting rings while superimposing the second strip-shaped film on the first strip-shaped film to which the rings are fixed.

In general, the first strip-shaped film, the strip-shaped film for rings and the second strip-shaped film would be subjected to the above-described work while being unwound from a first film roll, a film roll for rings and a second film roll, respectively.

In a preferred embodiment, a boundary line is formed intermediate the rings.

The boundary line preferably is a discontinuous cutting line.

In accordance with the present invention, the chain of interconnected covers can be manufactured while the first strip-shaped film, the strip-shaped film for rings and the second strip-shaped film are made to travel in continuous fashion. This makes it possible to raise productivity and provide the cover at low cost.

Furthermore, the present invention provides a cover attaching stand ideal for use when the above-described probe cover is fitted over the sensor probe.

The cover attaching stand includes a base plate, which is held by legs or walls at a position having a prescribed height, for allowing a probe cover to be placed thereon, the base plate having a probe insertion hole of a size corresponding to the inner diameter of the fitting ring.

The diameter of the probe insertion hole generally would be slightly larger than the inner diameter of the fitting ring.

When the probe cover is fitted over the probe using the cover attaching stand, first the probe cover is placed on the base plate with the second film being placed on the upper side, and the cover is positioned in such a manner that the ring of the cover is made to substantially agree with the position of the insertion hole in the base plate. The probe is then inserted in the ring from above the second film. At this time the ring is reliably supported at the portion of the base plate where the periphery of the insertion hole is located. As a result, the probe can be advanced into the ring without causing the ring to deform. If the ring is fitted into or engaged with the probe, the fitting of the cover on the probe is finished. The probe then need only be raised from the insertion hole.

When the cover attaching stand according to the present invention is used in this manner, the probe cover can be attached to the probe with facility.

The present invention further provides a cover accommodating case in which the above-described chain of interconnected covers is placed in advance, the case being suitable for fitting a cover, which is contained in the chain of interconnected covers, over a probe.

The cover accommodating case has a case body defined by side walls and a bottom wall, and a lid provided on the case body, so as to be free to open and close, in such a manner that at least a portion of an opening in a top side of the case body is covered, the lid being formed to have a sensor probe insertion hole of a size corresponding to the inner diameter of the rings provided on the chain of interconnected covers accommodated within the case body, and a guide for pulling out the chain of interconnected covers accommodated within the case body.

The cover accommodating case can be expressed as follows: Specifically, the cover accommodating case according to the present invention comprises a case body defined by side walls and a bottom wall, and a lid provided on the case body, so as to be free to open and close, in such a manner that at least a portion of an opening in a top side of the case body is covered, the lid being formed to have a sensor probe insertion hole of a size corresponding to the inner diameter of the rings provided on the chain of interconnected covers accommodated within the case body, and the opening in the top side of the case body not covered by the lid or an opening formed in the lid serving as an aperture for pulling out the chain of interconnected covers accommodated within the case body.

A first feature of the cover accommodating case is that the chain of interconnected covers can be accommodated within the case.

A second feature is that a portion of the chain of interconnected covers, which is accommodated within the case, substantially corresponding to one cover can be pulled out along the above-mentioned guide or through the above-mentioned aperture and supplied in order to be fitted over the probe by being placed upon the lid with the second strip-shaped film on the upper side. The fitting of a portion corresponding to one cover over the probe is carried out by passing the tip of the probe through the ring from above the second strip-shaped film in a state in which the ring of the portion corresponding to one cover has been made to coincide with the probe insertion hole of the lid, in the same manner as in the case of the above-described stand for attaching the cover.

After the portion corresponding to one cover has been fitted over the probe, the latter is withdrawn upwardly from the insertion hole and the chain of interconnected covers is pulled out of the interior of the case by an amount equivalent to one cover. If the boundary between the portion fitted on the probe and the cover portion that has been pulled out is cut, this will complete the operation for attaching the cover.

If a cutting line is formed along the boundary between the covers of the chain of interconnected covers in the manner described above, the attached cover can be severed from the chain of interconnected covers with ease.

According to a preferred embodiment of the invention for the purpose of facilitating this severing operation, a guide is molded in a portion facing the opening in the upper side of the case body not covered by the lid or the opening formed in the lid. A retaining member is provided on the case body in a freely erectable manner so as to cover this opening and overlap a part of the cover.

If a portion connected to the chain of interconnected covers inside the case is pressed by this retaining member, only the cover that has been fitted over the probe can be readily severed and detached at the location of the cutting line.

One more advantage of the cover accommodating case is that the cover can be fitted over the probe and the fitted cover can be severed from the chain of interconnected covers without the hand of the user touching the cover and the probe. This is highly hygienic.

A cover accommodating case according to one more embodiment provided by the present invention comprises a case body defined by side walls and a bottom wall, and a lid provided on the case body, so as to be free to open and close, in such a manner that at least a portion of an opening in a top side of the case body is covered, the lid being formed to have a cut-out, for sensor probe insertion, having a width corresponding to the inner diameter of rings provided on a chain of interconnected covers, which is accommodated within the case body, and extending to one side wall, and the one side wall being formed to have a cut-out for guiding a sensor probe, which has been inserted into the cut-out for sensor probe insertion, to the outside of the case.

When this cover accommodating case is used, one cover connected to the chain is fitted over the probe, after which the probe can be pulled out in the horizontal direction through the cut-out in the one side wall of the case. This greatly facilitates operability in terms of fitting the cover over the probe.

It goes without saying that this cover accommodating case also can be provided with the retaining member.

Other features and advantages of the present invention will become more apparent from a description of embodiments made with reference to the drawings.

BRIEF DESCRIPTION OF THE DRAWINGS

FIGS. 4 and 5 illustrate a cover attaching stand, in which FIG. 4 is a plan view and FIG. 5 a side view;

FIGS. 7, 8 and 9 illustrate a process for manufacturing the chain of interconnected covers, in which FIG. 7 is a perspective view showing the first half of the process, FIG. 8 a plan view of a strip-shaped film for rings and FIG. 9 a perspective view showing the second half of the process;

FIGS. 10 through 13 illustrate a cover accommodating case, in which:

FIG. 10 is a side view of the cover accommodating case;

FIG. 11 is a plan view of the cover accommodating case;

FIG. 12 is a sectional view taken along line XII—XII of FIG. 11; and

FIG. 13 shows a front side and a back side of the cover accommodating case, in which the right half illustrates the front and the left half illustrates the back;

FIGS. 14a through 14d show a procedure for fitting a cover over the sensor probe using the cover accommodating case; and FIGS. 15 through 17 illustrate another embodiment of the cover accommodating case, in which:

FIG. 15 is a plan view of the cover accommodating case;

FIG. 16 is a sectional view of the cover accommodating case; and

FIG. 17 is a front view of the cover accommodating case.

BEST MODE FOR CARRYING OUT THE INVENTION

Figure 1:
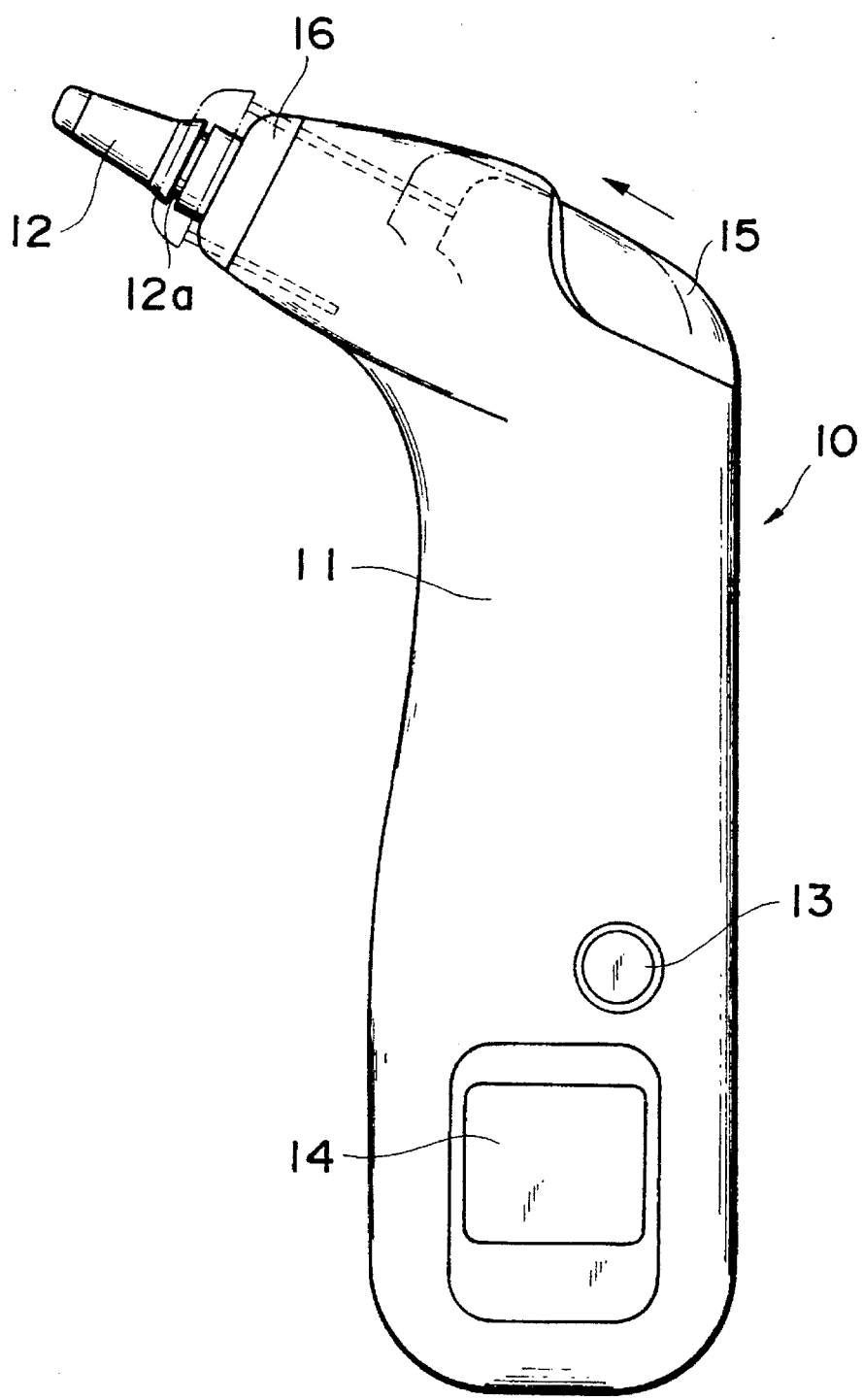
FIG. 1 is a front view illustrating the entirety of an infrared thermometer.

FIG. 1 illustrates the external appearance of an infrared thermometer.

An infrared thermometer 10 has a case 11 made to have a shape suitable for being grasped by the hand. The tip of the case 11 is curved at an inclined angle and is provided with a probe 12. The tip of the probe 12 is open and the interior of the opening accommodates a radiant-temperature sensor (not shown). Incident infrared radiation from the opening of the probe 12 is sensed by the temperature sensor. The output signal of the temperature sensor is applied to a temperature measurement circuit provided inside the case 11. The temperature is determined by the temperature measurement circuit. The temperature determined is displayed on a liquid-crystal display device 14 provided on the base portion of the case 11. The base portion of the case 11 is further provided with a power-supply switch 13.

The probe 12 is shaped so that its cross section is circular, with the probe narrowing toward its tip. The base portion of the probe 12 is formed to have an annular groove 12a, which is useful for securing a probe cover described later. The periphery of the base portion of probe 12 is provided with a release pipe 16 that is free to advance and retract. The release pipe 16 ordinarily is in the retracted position and is made to project, as indicated by the chain line, by pressing a release button 15 in the direction of the arrow. The release pipe 16 is useful for removing a cover that has been attached to the probe 12.

Figure 2:
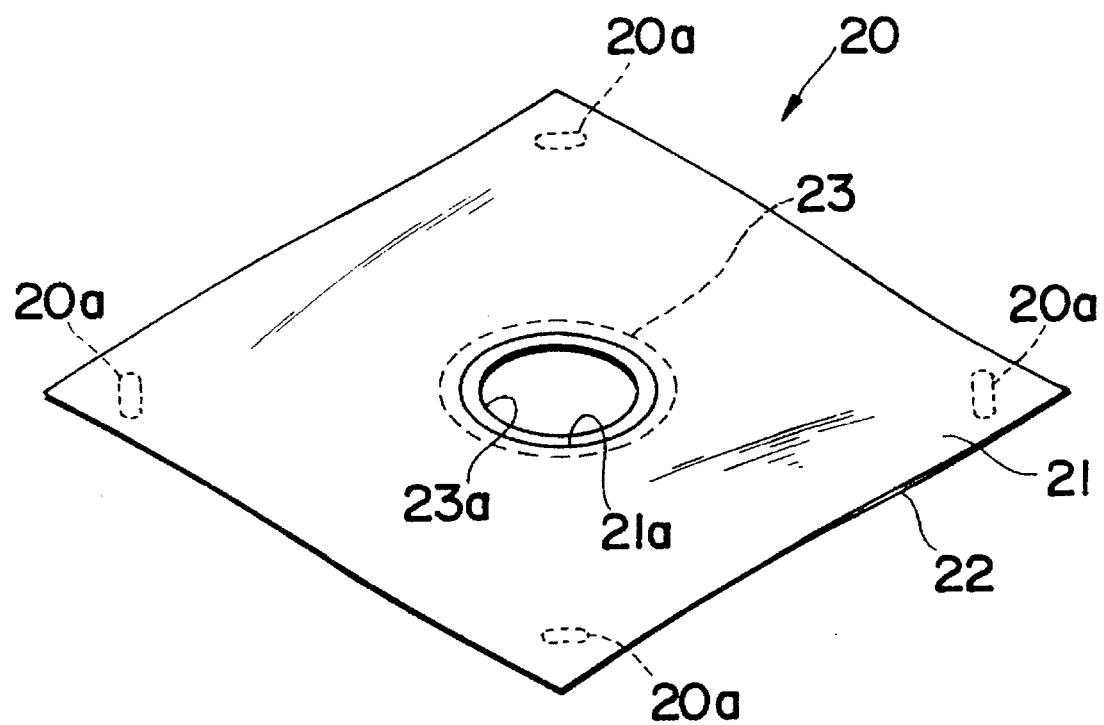
FIG. 2 is a perspective view illustrating the probe cover.

FIG. 2 illustrates the probe cover.

A probe cover 20 comprises two substantially square films 21 and 22 and a ring 23. The first film 21 is provided with a hole 21a in the center thereof. The ring 23, which has a hole 23a, is thermally fused to the inner side of the first film 21. The centers of the holes 21a and 23a substantially coincide. The holes 21a and 23a are of approximately the same size, though it is preferred that the hole 23a of ring 23 be slightly smaller than the hole 21a. The first film 21 and the second film 22 are thermally fused together at the locations (indicated at 20a) of their four corners.

The material of the probe cover 20 to be fitted over the probe 12 of the infrared thermometer is such that the second film 22 is transparent to infrared radiation. Though the material of the first film 21 is not a problem, the materials of both films 21 and 22 should be made the same in order to raise the productivity of the probe cover. The films 21 and 22 preferably are transparent. The ring 23 is thicker and harder than the films 21, 22. The ring 23 may be affixed to the outer side of the film 21 rather than the inner side thereof.

Figure 3A:
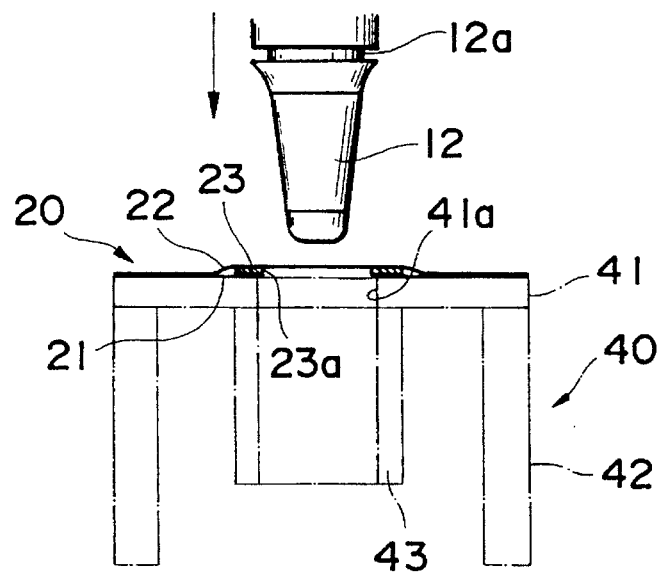
FIGS. 3a and 3b are sectional views illustrating a procedure for fitting a cover over a probe.
Figure 3B:
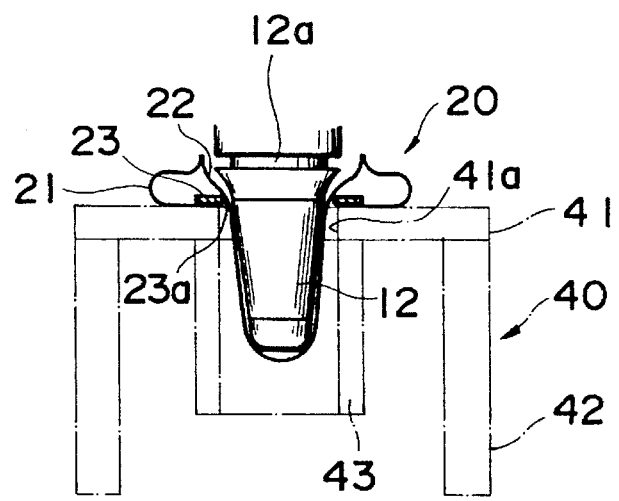
Figure 4:
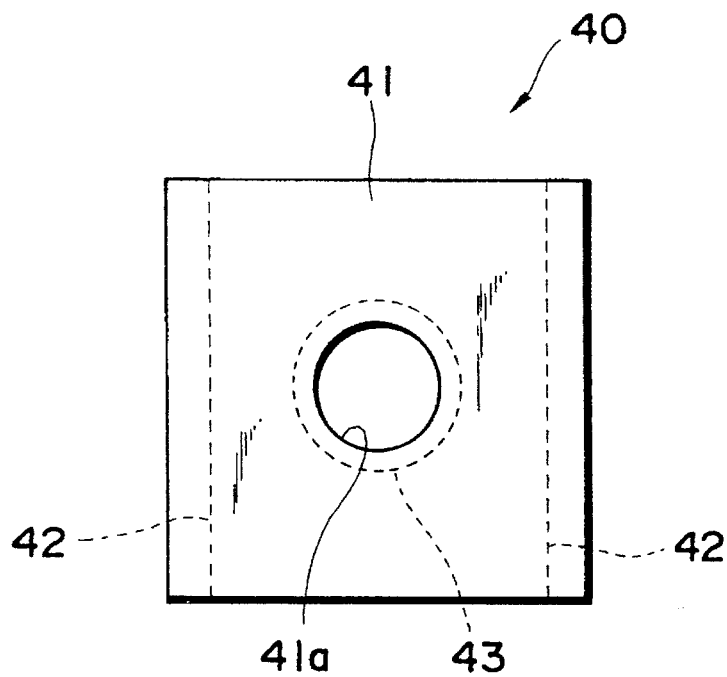
Figure 5:
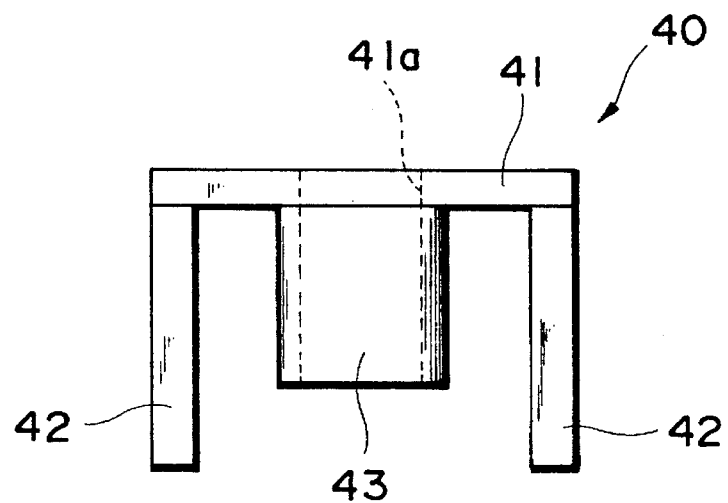

FIGS. 3a and 3b illustrate a method of fitting the above-described probe cover 20 over the probe 12 of the infrared thermometer. It is preferred that use be made of a cover attaching stand 40 of the kind shown in FIGS. 4 and 5.

The cover attaching stand 40 comprises a base plate 41 and legs 42 supporting the base plate 41. The base plate 41 is provided with a probe insertion hole 41a. A cylinder 43 having a space communicating with the insertion hole 41a is secured to the underside of the base plate 41. The cylinder 43 is for guiding the probe 12. The inner diameter of the probe insertion hole 41a is slightly larger than the inner diameter of the hole 23a of the ring 23 of cover 20.

With reference now to FIG. 3a, the probe cover 20 is placed upon the base plate 41 of the cover attaching stand 40 with the first film 21 disposed on the lower side, and the cover is so arranged that the center of the ring 23 and the center of the insertion hole 41a substantially coincide.

With reference to FIG. 3b, the probe 12 of the infrared thermometer is pressed into the ring 23 from above the second film 22 of the cover 20. When this is done, the second film 22 on the upper side covers the tip of the probe 12 while it is folded back as the tip of the probe 12 penetrates the ring 23, the hole 41a and the interior of the cylinder 43. The film 21 on the lower side also is pulled by the film 22 on the upper side and therefore is deformed. If the probe 12 is pushed in further, the ring 23 fits into the annular groove 12a at the base portion of the probe. As a result, the probe 12 is completely covered by the cover 20, especially the second film 22, thereby completing the preparations for measurement of body temperature.

The ring 23 is for assuring that the cover 20 fitted onto or engaged with the base portion of the probe 12 will not readily become detached. Accordingly, the shape and size of the hole 23a are decided in dependence upon the shape and size of the location on the probe 12 that mates with the ring.

The probe attaching stand 40 supports the cover 20 inclusive of the ring 23. In particular, the insertion hole 41a of the base plate 41 should support the ring 23 of cover 20 against the insertion of the probe 12. Accordingly, the shape of the insertion hole 41a is not limited to a circular shape but may be triangular or rectangular. The legs 42 of the attaching stand 40 should hold the base plate 41 at a position whose height is greater than the length of the probe 12.

The probe 12 over which the cover 20 has been fitted in the manner described above is inserted into the ear canal so that body temperature can be measured through a prescribed operating procedure. If the release button 15 is pressed in the direction of the arrow in FIG. 1 after the end of body temperature measurement, the release pipe 16 thrust forward to forcibly detach the ring 23 of the cover 20 from the annular groove 12a. The cover 20 is removed from the probe 12 as a result.

Figure 6:
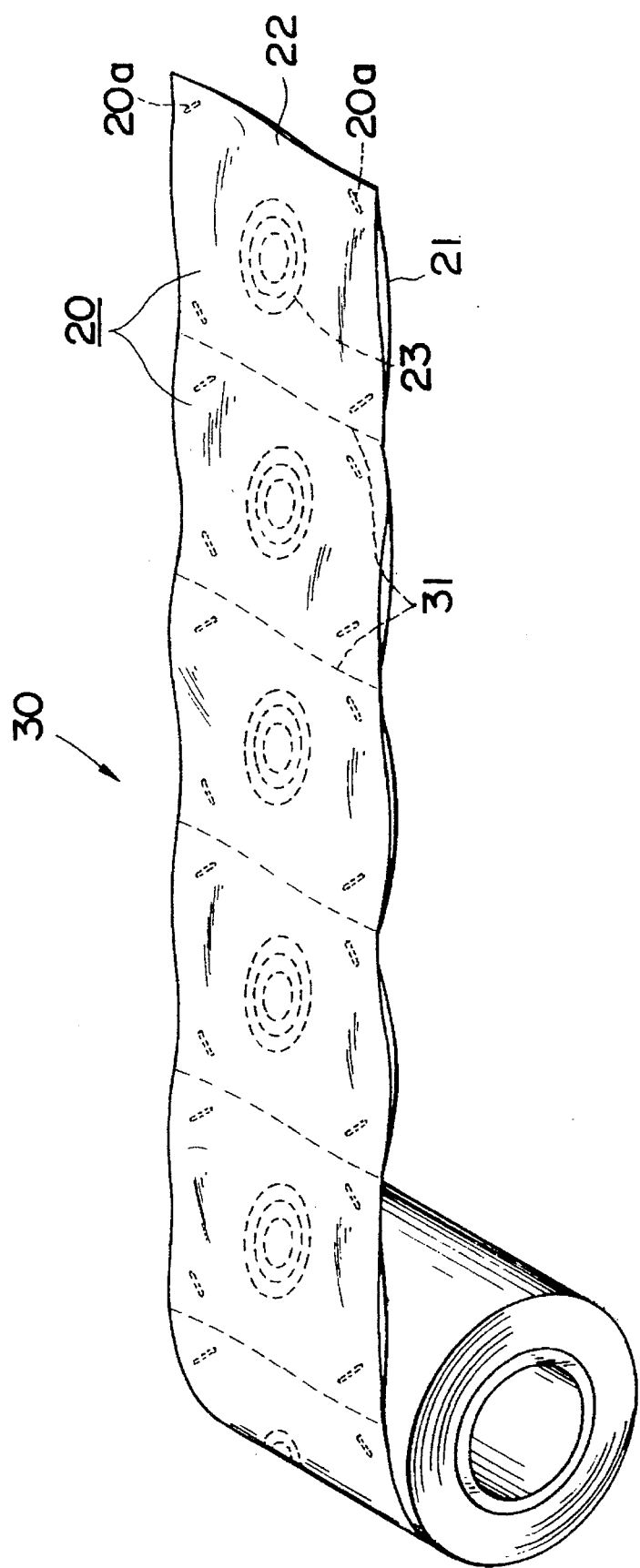
FIG. 6 is a perspective view illustrating a chain of interconnected covers.

FIG. 6 illustrates a chain of interconnected covers.

A chain of interconnected covers 30 consists of a plurality of the probe covers 20, shown in FIG. 2, linked successively into the form of a strip. The boundary between neighboring covers 20 is provided intermittently with a cutting line (slits) (so-called perforations) 31. This makes it possible to separate individual covers 20 from the chain 30 with facility. It is preferred that the chain of interconnected covers 30 be supplied in a form wound upon a cylindrical core.

Figure 7:
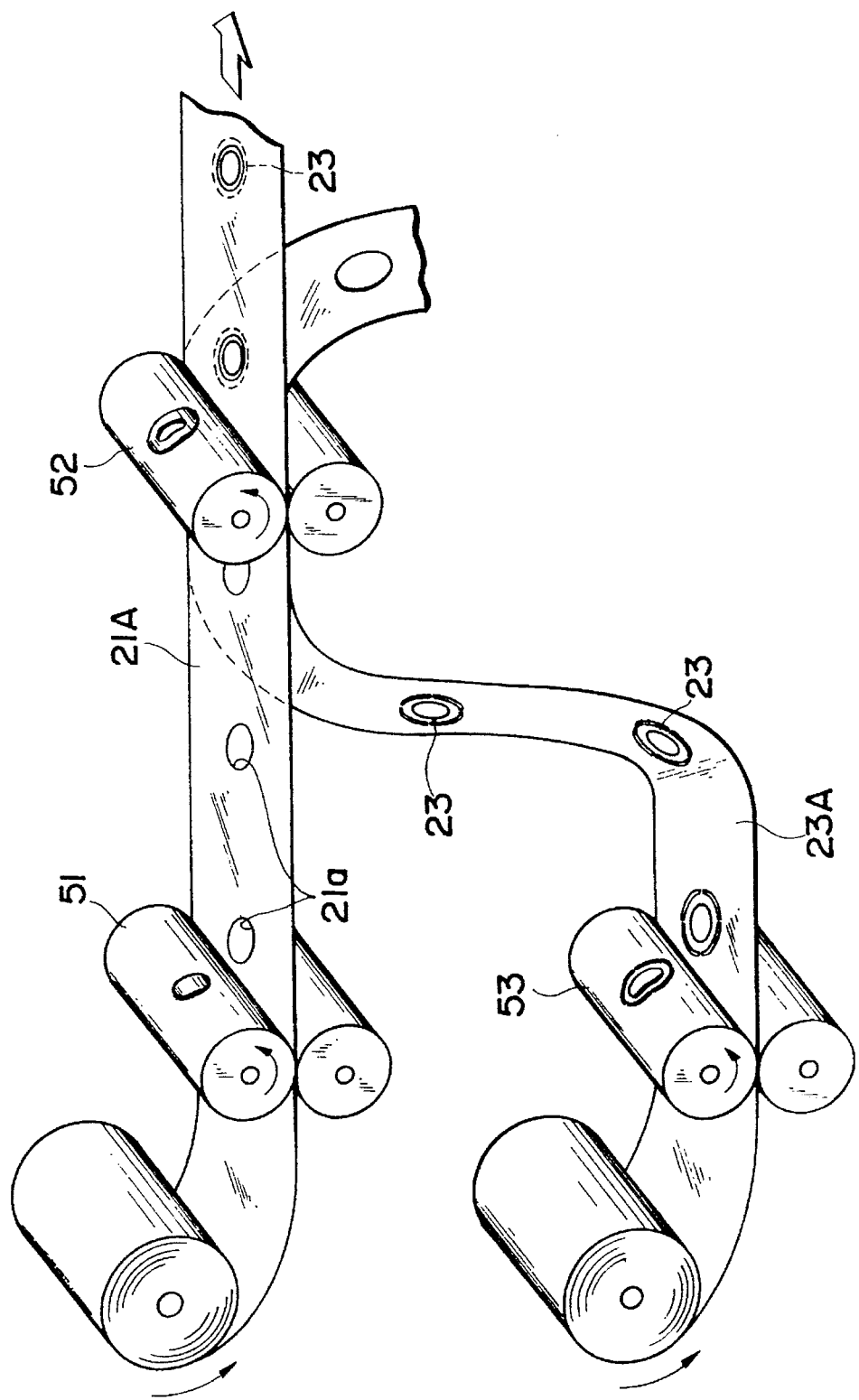
Figure 8:
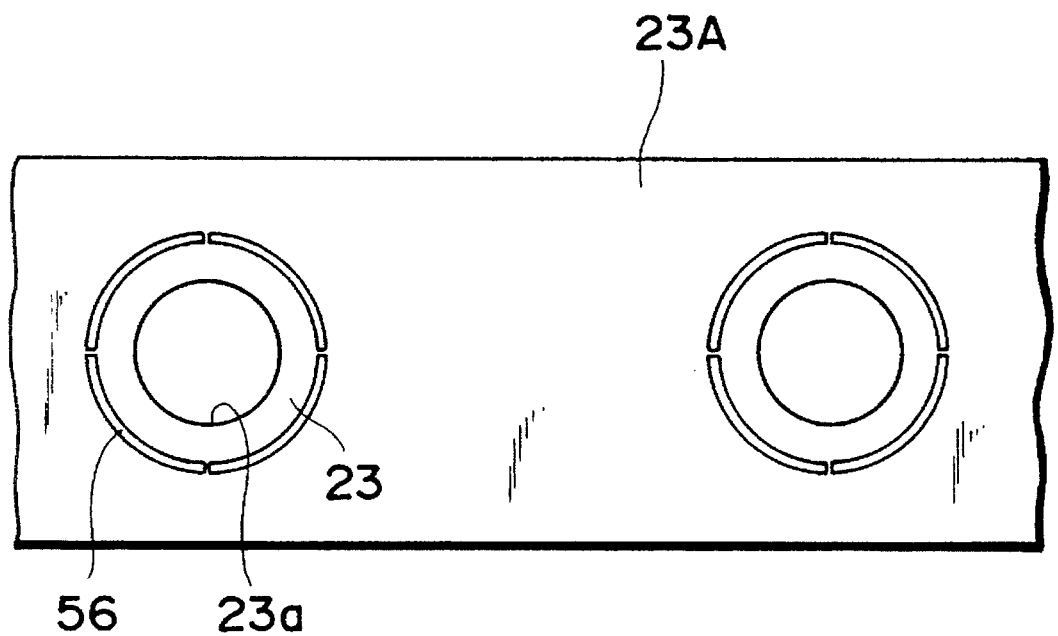
Figure 9:
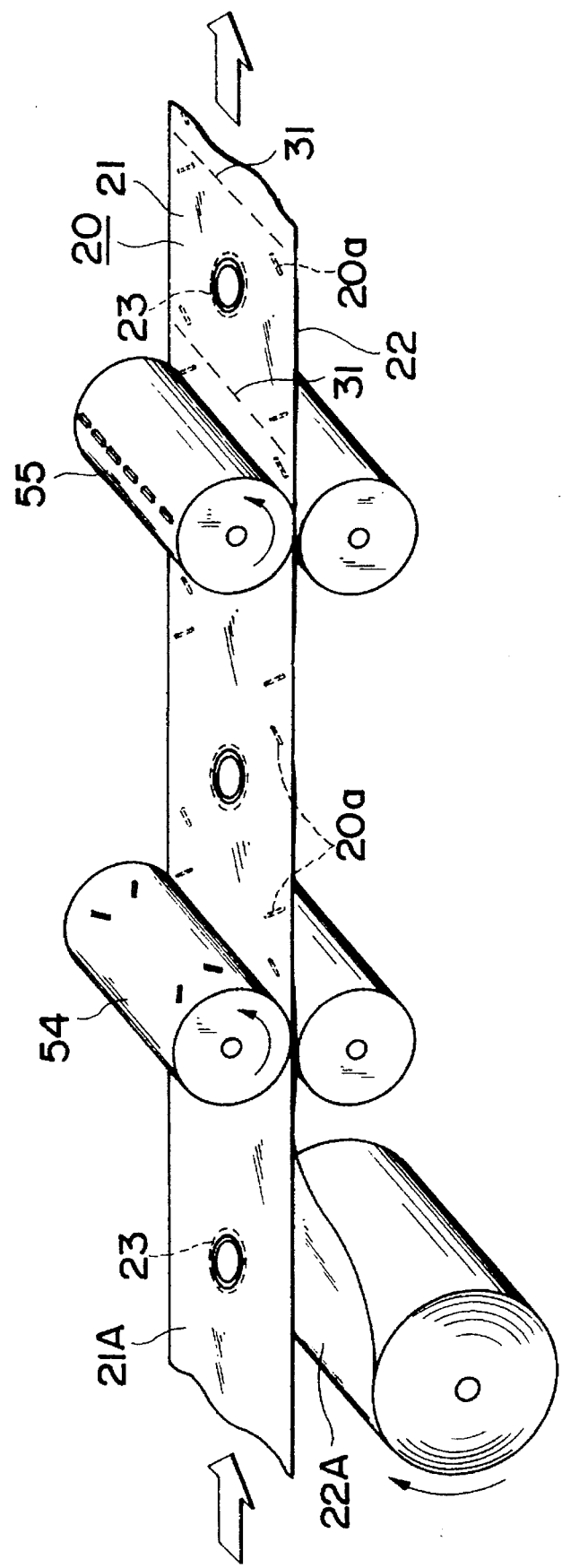
Figure 10:
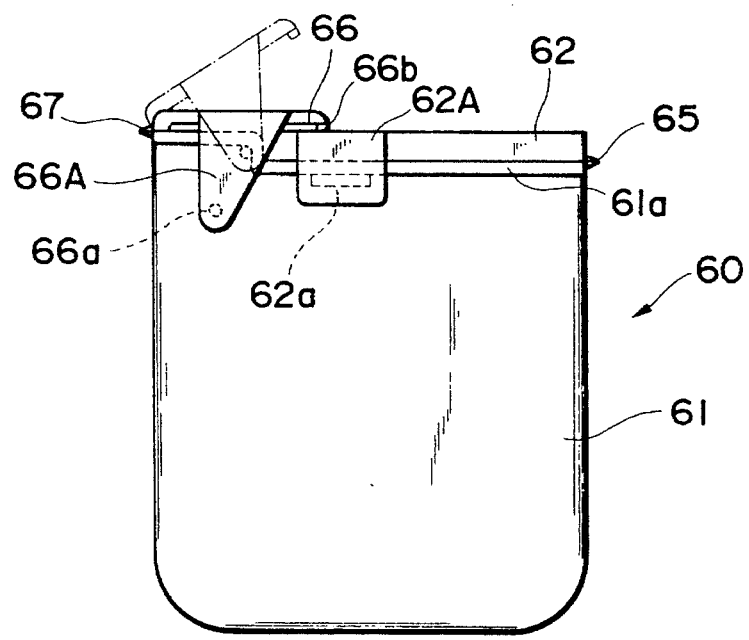
Figure 11:
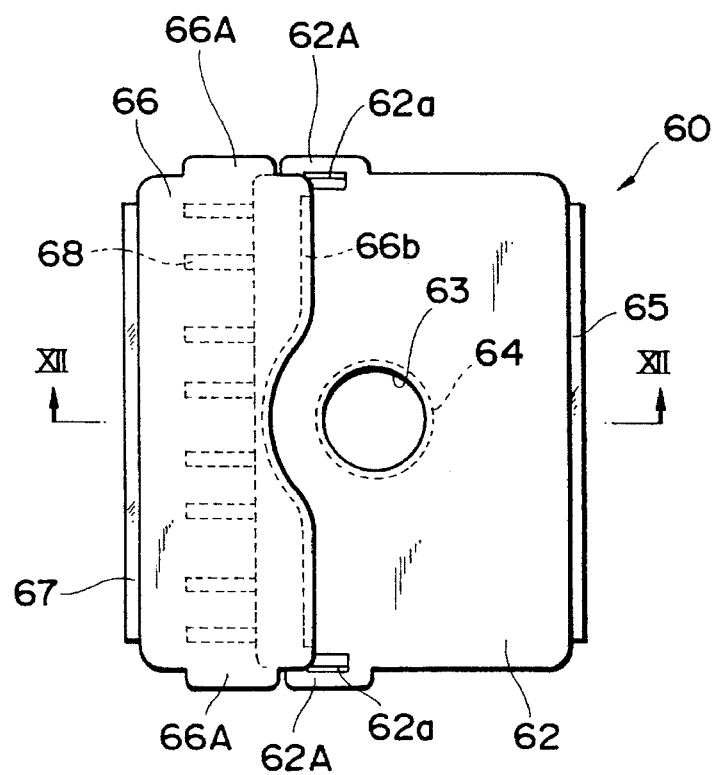
Figure 12:
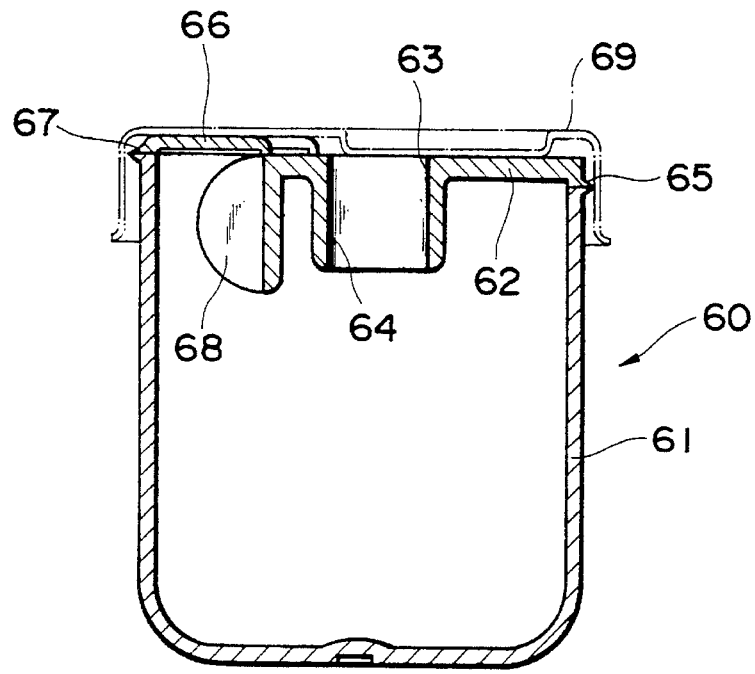
Figure 13:
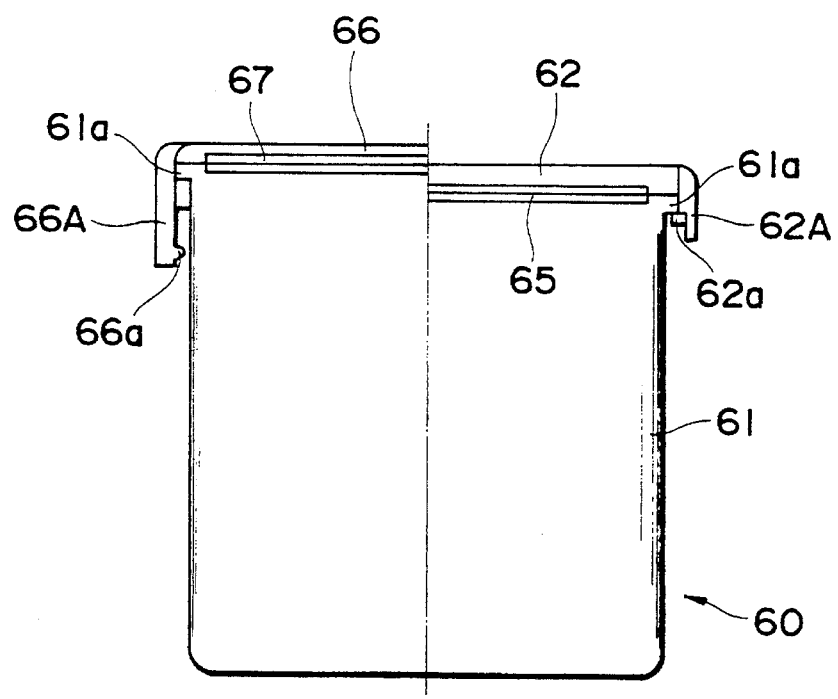

FIGS. 7 through 9 illustrate a method of manufacturing the chain of interconnected covers.

With reference to FIG. 7, a first strip-shaped film 21A unwound from a first film roll and a strip-shaped film 23A for rings unwound from a film roll for rings are processed while traveling along respective travel paths.

The first strip-shaped film 21A is provided with first holes 21a at regular intervals by a roller 51 equipped with a hole forming cutter.

The strip-shaped film 23A for rings is formed to have the rings 23 at regular intervals equal to those of the first holes 21a by a roller 53 equipped with a ring forming cutter. As shown in FIG. 8, each ring 23 has the hole 23a on its inner side, and the outer periphery of the ring is defined by a plurality of arcuate slits 56. The ring 23 is connected to the film 23A by the portions at which the slits 56 are discontinuous. Since these connecting portions are very small, the ring 23 is capable of being detached from the film 23A with ease.

The first strip-shaped film 21A formed to have the holes 21a and the strip-shaped film 23A for rings formed to have the rings 23 are superimposed at the position of a roller 52 in such a manner that the holes 21a and the holes 23a of the rings 23 substantially coincide. By virtue of the roller 52, which has a ring-shaped heating portion for thermal fusion, the rings 23 are fused onto the periphery of the holes 21a of the strip-shaped film 21A in the course of passing by the position of the roller 51, and the rings 23 are detached from the strip-shaped film 23A for the rings.

Next, as shown in FIG. 9, a second strip-shaped film 22A unwound from a second film roll is introduced to the path of travel of the first strip-shaped film 21A onto which the rings 23 have been fused. As both films 21A and 22A travel while superimposed, they are fused together at four locations approximately midway between the rings 23 by a roller 54 having a plurality of heating portions for fusing purposes. In other words, fused sites 20a are formed.

Furthermore, intermittent slits 31 are provided in the width direction at positions exactly midway between the rings 23 by a roller 55 having a cutter (a perforation cutter) arrayed intermittently in a single row. The positions of the slits 31 are the boundary lines of the individual covers 20.

Predetermined lengths of the chain of interconnected covers thus manufactured are wound into individual rolls to obtain the final product.

Thus, the hole forming roller, the ring forming roller, the fusing roller and the roller having the perforation cutter are arranged so as to form a line, and the chain of interconnected covers is manufactured while the strip-shaped films serving as the material travel along the line. The result is improved productivity.

FIGS. 10 through 13 illustrate a cover accommodating case suitable for accommodating the chain of interconnected covers 30 manufactured as set forth above and for fitting a part of the chain 30 over the probe of the infrared thermometer while the chain is pulled out.

A cover accommodating case 60 is made of a synthetic resin such as plastic and comprises a case body 61, a lid 62 attached to one side of the top of the case body 61 so as to be free to open and close, and a retaining member 66 provided on the other side of the top of the case body in a freely erectable manner.

The case body 61 comprises four side surfaces and a bottom surface and has a hollow interior capable of accommodating the product, namely the chain of interconnected covers wound in roll form.

The lid 62 is attached by a hinge 65 to the upper end of one side wall (this shall be referred to as the front side) of the case body 61 so as to be free to open and close. The hinge 65 comprises a comparatively thin-walled portion connected to the side wall. The lid 62 is sized to cover substantially two-thirds to three-fourths of the opening in the top side of the case body 61; the portion of the opening not covered by the lid 62 is left in the top side of the case body 61.

The lid 62 is provided with a probe insertion opening 63 at a location situated substantially in the center as seen from the top side of the case body 61. The insertion opening 63 is larger than the hole 23a in the ring 23 of the cover 20. A cylindrical portion 64 extends downward from the peripheral portion of the insertion hole 63. Furthermore, a downwardly extending guide 68 is integrally formed on the edge of the lid 63 on the side thereof opposite the hinge 65. The guide 68 includes a plurality of semicircular fins provided in parallel and is for the purpose of allowing the chain of interconnected covers 30 accommodated within the case main body 61 to be pulled out smoothly to the top side of the lid 62 from inside the case body 61.

The upper ends of the side walls of the case body 61 (the wall surfaces perpendicular to the front wall on which the hinge 65 is provided) are slightly lower (by an amount equivalent to the thickness of the lid 62) at the portion covered by the lid 62 and slightly higher at the portion not covered by the lid 62. These wall portions are formed to have flanges 61a, which project outwardly a small amount, along their upper edges. Pieces 62A extend downwardly from portions on both sides of the lid 62, and an engaging projection 62a is provided on the inner side of each piece 62A. The projection 62a engages the lower side of the flange 61a when the lid 62 is closed, whereby the lid 62 is held in the closed state.

The retaining member 66 is attached, so as to be free to open and close, on the upper end of the back wall of the case body 61 by a hinge 67. This hinge 67 also comprises a thin-walled portion formed as an integral part of the case body 61, just as in the case of hinge 65. Accordingly, the retaining member 66 is biased upward, in the upstanding direction, owing to the resilience possessed by the hinge 67. When the retaining member 66 is closed it covers the portion of the opening not covered by the lid 62 of case body 61 and overlaps part of the lid 62.

Both sides of the retaining member 66 also are provided with downwardly extending pieces 66A, each of which has an engaging projection 66a formed on the lower portion of its inner side. The projections 66a are spaced away from the flanges 61a when the retaining member 66 is in the closed state. As indicated by the chain line in FIG. 10, the projections 66a act to limit the angle through which the retaining member 66 is erected. That is, the projections 66a engage with the flanges 61a when the retaining member 66 is in a state in which it has been erected through a certain angle.

The lower surface at the edge of the distal end of the retaining member 66 is formed to have a small retaining rib 66b which abuts against the upper surface of the lid 62 when the retaining member 66 is closed.

Furthermore, a cover 69 (see FIG. 12) is provided to cover the case body 61 when the lid 62 and retaining member 66 are in the closed state.

The method of using the cover accommodating case 60 is illustrated in FIGS. 14a through 14d.

First, the chain of interconnected covers 30 wound into the form of a roll is placed inside the cover accommodating case 60 as a preparatory step. The cover 69 of the case 60 is removed, the retaining member 66 and the lid 62 are opened, the roll-shaped chain of interconnected covers 30 is placed inside the case 60 and part of the chain is pulled out. The lid 62 is closed and the retaining member 66 is placed in the half-open state (a state in which the engaging projections 66a are engaged with the flanges 61a). The part of the chain of interconnected covers 30 that has been pulled out is placed upon the lid 62. It is required that the chain of interconnected covers 30 be accommodated within the case 60 in such a manner that the first film 21 is disposed on the lower side and the second film 22 on the upper side on the lid 62.

The hole 23a of one of the rings 23 on part of the chain of interconnected covers 30 (namely the part corresponding to a single probe cover 20) pulled out onto the lid 62 is placed in a state in which it is substantially registered with the insertion hole 63 in the lid 62 (see FIG. 14a).

The probe 12 of the infrared thermometer 10 is pressed into the hole 23a of the ring 23 from above the second film 22 (see FIG. 14b) in the same manner as set forth in the cover attaching method described above. When the ring 23 fits into the annular groove 12a of the probe 12, this means that the cover 20 has been fitted over the probe 12.

The probe 12 is raised and pulled out of the insertion hole 63 after the cover 20 has been fitted on the probe. The probe 12 is then moved substantially horizontally to pull the chain of interconnected covers until the boundary line between the attached cover 20 and the next adjacent cover arrives at the front edge of the lid 62 (see FIG. 14c).

The retaining member 66 is pressed down to clamp part of the chain of interconnected covers 30 on the lid 62 between itself and the lid 62. If the probe 12 is now pulled further to the side under these conditions, the intermittent slits forming the boundary line tear so that the cover 20 that has been fitted over the probe 12 is detached from the chain 30 (see FIG. 14d).

If the distance from the center of the ring 23 in the cover 20 to the edge of one side of the cover 20 and the distance from the center of the insertion hole 63 in the lid 62 of the case 60 to the front edge of the case 60 are made approximately equal, then the ring 23 of the next cover 20 remaining on the lid 62 will assume a state in which it substantially coincides with the insertion hole 63 in the lid 62. This makes it possible to prepare for the fitting on of the next cover.

Figure 15:
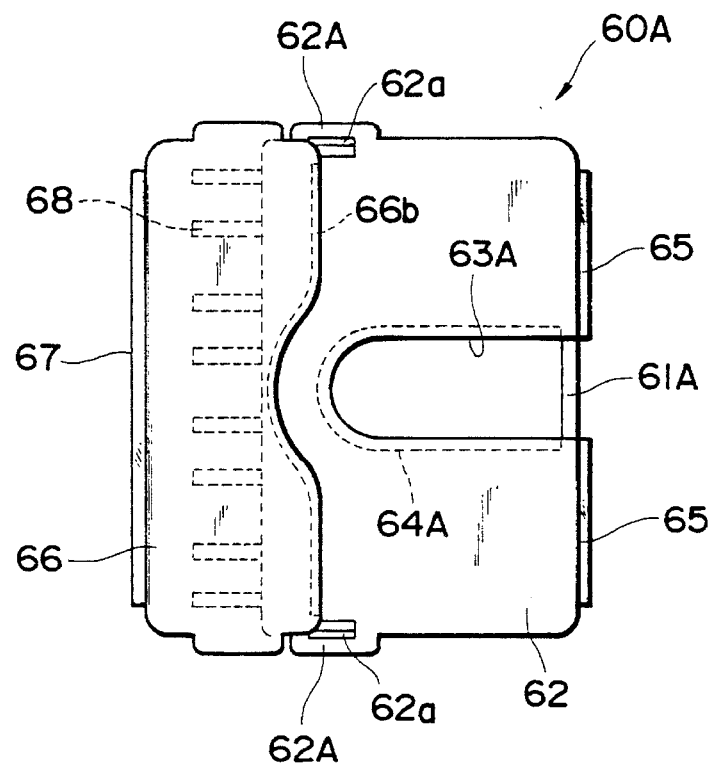
Figure 16:
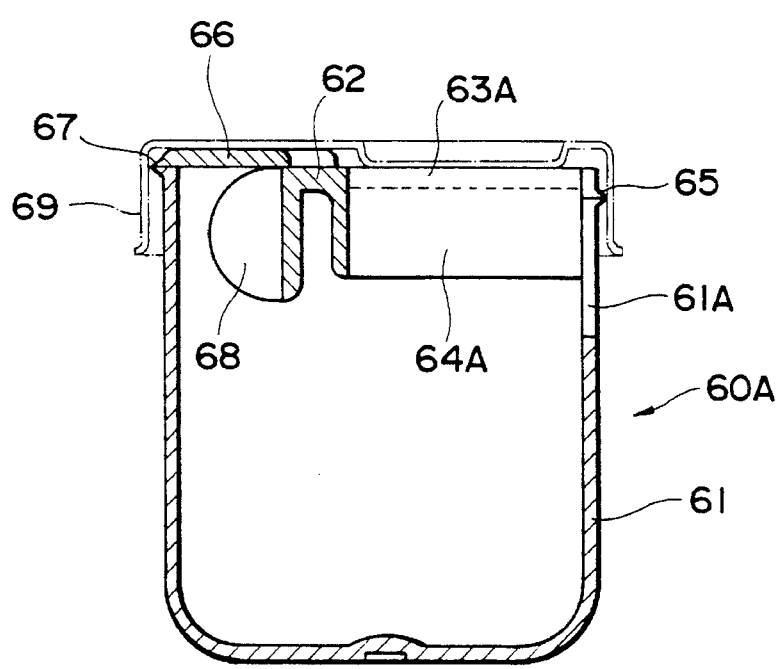
Figure 17:
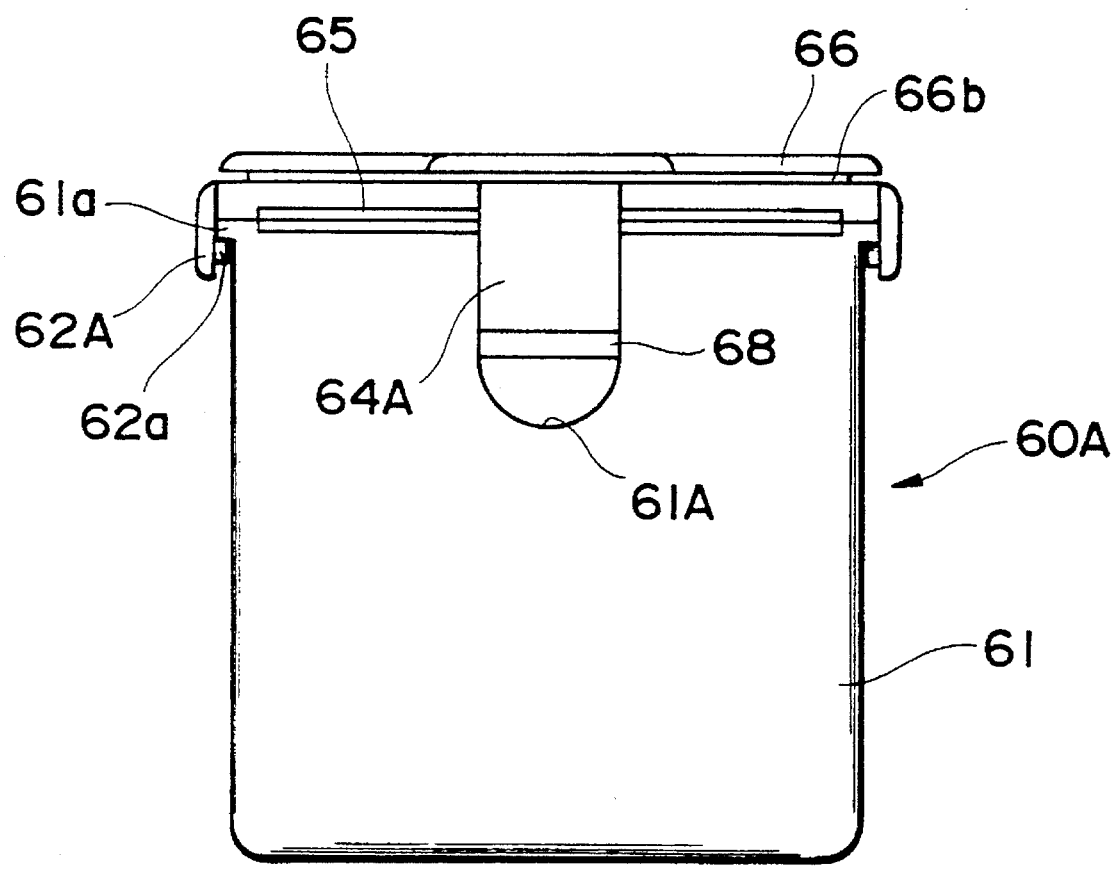

FIGS. 15 through 17 illustrate another embodiment of the cover accommodating case. Components in these drawings identical with those shown in FIGS. 10 through 13 are designated by like characters and need not be described again.

In this cover accommodating case indicated at 60A, the lid 62 is formed to have a U-shaped cut-out 63A instead of the circular probe insertion hole. Further, the front wall of the case body 61 is formed to have a U-shaped cut-out 61A that communicates with the cut-out 63A.

The cut-out 63A allows the probe 12 to be pressed into the ring 23 of the cover 20 when the cover is fitted over the probe. It also allows the probe 12 fitted with the cover 20 to be pulled out of the case. The cut-out 61A also allows the probe 12 to be pulled out of the case.

More specifically, according to this embodiment, after the cover 20 has been fitted over the probe 12, the probe 12 can be withdrawn from case 60A merely by moving the probe 12 in the horizontal direction without it being lifted. This greatly facilitates the operation for fitting on the cover.

Industrial Applicability

The speculum cover including the probe cover of the infrared thermometer, the method of manufacturing the speculum cover and the cover accommodating case are capable of being utilized in the medical equipment industry.

What is claimed is:

1. A sensor probe cover comprising:

a first film formed to have a first hole at a central portion thereof;

a fitting ring fixed to a periphery of the first hole of said first film and having a second hole configured to be fitted on a sensor probe to which the cover is to be attached;

a second film overlapping one side of said first film and bonded to said first film at a plurality of locations and not bonded to said fitting ring, wherein a portion of said second film that is larger in unstretched surface area than an area of the second hole and is not bonded to said first film is available to pass through said second hole to cover a sensor probe without substantial stretching.

2. The cover according to claim 1, wherein said first film and said second film are bonded at a plurality of locations substantially equidistant from the center of said fitting ring and spaced apart substantially equiangularly.

3. The cover according to claim 1, wherein said first film and said second film are rectangular and are bonded together at their four corners.

4. The cover according to claim 1, wherein said second film exhibits transparency to infrared radiation so as to be suitable for being fitted over the sensor probe of an infrared thermometer.

5. A sensor probe cover comprising:

a flexible support member formed to have a hole configured to be fitted on a sensor probe to which a cover is to be attached; and a film superimposed on said support member and bonded to said support member at a plurality of locations, wherein a portion of the film that is larger in unstretched surface area than an area of the hole and is not bonded to said support member is available to pass through the hole to cover a sensor probe without substantial stretching.

6. The cover according to claim 5, wherein at least a periphery of said hole of said support member is more rigid than said film.

7. The cover according to claim 5, wherein said support member comprises a film formed to have a first hole at a central portion thereof; and a fitting ring fixed to a periphery of the first hole of this film and having a second hole suitable for being fitted on the sensor probe to which the cover is to be attached.

8. The cover according to claim 5, wherein said support member and said film are bonded at a plurality of locations substantially equidistant from the center of said hole and spaced apart substantially equiangularly.

* * * * *